(12) United States Patent
Lu et al.

(10) Patent No.: US 11,065,241 B2
(45) Date of Patent: Jul. 20, 2021

(54) PHARMACEUTICAL COMPOSITION COMPRISING QUINOLINE DERIVATIVE OR SALT THEREOF

(71) Applicant: Jiangsu Hengrui Medicine Co., Ltd., Jiangsu (CN)

(72) Inventors: Yun Lu, Jiangsu (CN); Xinhua Zhang, Jiangsu (CN); Chenyang Wang, Jiangsu (CN)

(73) Assignee: Jiangsu Hengrui Medicine Co., Ltd., Lianyungang (CN)

(*) Notice: Subject to any disclaimer, the term of this patent is extended or adjusted under 35 U.S.C. 154(b) by 409 days.

(21) Appl. No.: 16/071,157

(22) PCT Filed: Jan. 23, 2017

(86) PCT No.: PCT/CN2017/072155
§ 371 (c)(1),
(2) Date: Jul. 19, 2018

(87) PCT Pub. No.: WO2017/129087
PCT Pub. Date: Aug. 3, 2017

(65) Prior Publication Data
US 2020/0138803 A1 May 7, 2020

(30) Foreign Application Priority Data
Jan. 27, 2016 (CN) .......................... 201610056739.3

(51) Int. Cl.
*A61K 31/4709* (2006.01)
*A61K 47/32* (2006.01)
*A61K 9/20* (2006.01)
*A61K 9/48* (2006.01)

(52) U.S. Cl.
CPC .......... *A61K 31/4709* (2013.01); *A61K 47/32* (2013.01); *A61K 9/2018* (2013.01); *A61K 9/2027* (2013.01); *A61K 9/2054* (2013.01); *A61K 9/4866* (2013.01)

(58) Field of Classification Search
CPC .. A61K 31/4709; A61K 47/32; A61K 9/2018; A61K 9/2027; A61K 9/2054; A61K 9/4866
See application file for complete search history.

(56) References Cited

U.S. PATENT DOCUMENTS 9,309,226 B2 * 4/2016 Sun .......................... A61P 43/00

FOREIGN PATENT DOCUMENTS

| CN | 101824029 A | 9/2010 |
|----|-------------|--------|
| CN | 102675287 A | 9/2012 |
| CN | 102471312 B | 6/2014 |
| CN | 102933574 B | 10/2014 |
| CN | 103974949 B | 11/2015 |

OTHER PUBLICATIONS

Lieberman et al. ("Pharmaceutical Dosage Forms vol. 1" Marcel Dekker Inc., 1989, pp. i-xix, 1-593.*
Int'l Search Report dated Apr. 28, 2017 in Int'l Application No. PCT/CN2016/072155.
The second method (paddle method) of the dissolution rate test disclosed in the appendix of vol. II of Chinese Pharmacopeia (2010 edition).

* cited by examiner

*Primary Examiner* — Shirley V Gembeh
(74) *Attorney, Agent, or Firm* — Ice Miller LLP

(57) ABSTRACT

The present invention provides a pharmaceutical composition containing a quinoline derivative or a salt thereof. Specifically, the invention provides a pharmaceutical composition containing (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmaceutically acceptable salt thereof, a cross-linked polyvinylpyrrolidone, and at least one pharmaceutically acceptable excipient. The pharmaceutical composition has a property of rapid dissolution.

19 Claims, 4 Drawing Sheets

PHARMACEUTICAL COMPOSITION COMPRISING QUINOLINE DERIVATIVE OR SALT THEREOF

CROSS-REFERENCE TO RELATED APPLICATION

This application is a Section 371 of International Application No. PCT/CN2017/072155, filed Jan. 23, 2017, which was published in the Chinese language on Aug. 3, 2017, under International Publication No. WO 2017/129087 A1, which claims priority under 35 U.S.C. § 119(b) to Chinese Application No. 201610056739.3, filed Jan. 27, 2016, the disclosures of which are incorporated herein by reference in their entirety.

FIELD OF THE INVENTION

The present invention belongs to the field of pharmaceutical formulations, and specifically relates to a pharmaceutical composition comprising (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof. The pharmaceutical composition has a property of rapid dissolution.

BACKGROUND OF THE INVENTION

CN102471312B discloses a small molecule compound (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide that has a structure shown as formula I.

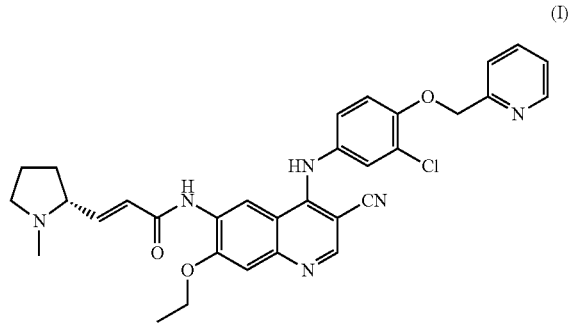 [SMILES: CCOc1cc2ncc(C#N)c(Nc3ccc(OCc4ccccn4)c(Cl)c3)c2cc1NC(=O)/C=C/[C@H]1CCCN1C]

(I)

It is known as a small molecule receptor tyrosine kinase inhibitor that inhibits epidermal growth factor receptor (EGFR) and human epidermal factor receptor 2 (ERBB2). It can covalently bind to the ATP binding sites of the kinase domains of EGFR and ERBB2 in cells, prevent the formation of homogeneous and heterogeneous dimers of EGFR and ERBB2 in tumor cells, inhibit their own phosphorylation, and block the activation of downstream signaling pathway, thereby inhibiting the growth of tumor cells. It can be clinically used for the treatment of various tumors such as gastric cancer, lung cancer, and breast cancer, etc.

CN102933574B discloses a maleate salt form of the compound of formula I that has advantages in terms of solubility, bioavailability and pharmacokinetics in comparison to other salts and the compound of formula I itself.

CN103974949B discloses crystal form I of dimaleate salt of the compound of formula I. This crystal form has good crystal stability and chemical stability, and can be used in the preparation of a medicament for treating diseases associated with EGFR receptor tyrosine kinase or HER-2 receptor tyrosine kinase.

However, when (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmaceutically acceptable salt thereof is prepared into a pharmaceutical solid composition, a high viscosity will be formed locally once the active ingredient is dissolved in water. It is not conducive to the preparation of the pharmaceutical formulation, and causes the decline in drug dissolution rate.

SUMMARY OF THE INVENTION

The object of the present invention is to provide a rapidly dissolving pharmaceutical composition. The process for preparing the pharmaceutical composition is simple and is more suitable for large-scale production.

The pharmaceutical composition provided by the present invention comprises an active pharmaceutical ingredient and cross-linked polyvinylpyrrolidone. The active pharmaceutical ingredient is (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof, for example hydrochloride salt, maleate salt, hydrobromide salt, p-toluenesulfonate salt, methanesulfonate salt, sulfate salt or ethanesulfonate salt, preferably maleate salt, and more preferably dimaleate salt. The active ingredient can be present in an amount of 5-70%, preferably 10-50%, and more preferably 20-40% by weight, relative to the total weight of the composition. The cross-linked polyvinylpyrrolidone can be present in an amount of about 2-20%, preferably 4-15% and more preferably 6-10% by weight, relative to the total weight of the composition.

The pharmaceutical composition provided by the present invention can also comprise a filler, for example one or more of microcrystalline cellulose, calcium hydrogen phosphate, mannitol, pregelatinized starch, and lactose, etc. The filler is present in an amount of about 5-80% by weight, relative to the total weight of the composition.

The pharmaceutical composition provided by the present invention can also comprise a binder, for example one or more of hydroxypropyl methyl cellulose, hydroxypropyl cellulose, sodium carboxymethyl cellulose, polyvinylpyrrolidone, and methyl cellulose, etc. The binder is present in an amount of about 0.5-15% by weight, relative to the total weight of the composition.

The pharmaceutical composition provided by the present invention can also comprise other disintegrant(s), for example one or more of croscarmellose sodium, sodium carboxymethyl starch, starch, and low-substituted hydroxypropyl cellulose, etc. The disintegrant is present in an amount of about 0-20% by weight, relative to the total weight of the composition.

The pharmaceutical composition provided by the present invention can also comprise one or more lubricant(s) that facilitates capsule filling or tableting. The lubricant includes talc, magnesium stearate, zinc stearate, glyceryl behenate, sodium lauryl sulfate, hydrogenated vegetable oil, colloidal silicon dioxide and the like. The lubricant is present in an amount of about 0.5-5% by weight, relative to the total weight of the composition.

The present invention also provides a pharmaceutical composition, comprising:

1) 5-70 wt % of (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof;

2) 2-20 wt % of cross-linked polyvinylpyrrolidone;

3) 5-80 wt % of a filler, wherein the filler is one or more selected from the group consisting of lactose and microcrystalline cellulose;

4) 0.5-15 wt % of a binder, wherein the binder is one or more selected from the group consisting of polyvinylpyrrolidone, hydroxypropyl methyl cellulose and hydroxypropyl cellulose; and 5) 0.5-5 wt % of a lubricant, wherein the lubricant is one or more selected from the group consisting of magnesium stearate and talc.

It can be seen from the dissolution test that due to the addition of cross-linked polyvinylpyrrolidone in the pharmaceutical composition of present invention, the dissolution rate of the active ingredient is greatly enhanced. The dissolution is rapid and complete, which is advantageous for the drug to enter the body to work quickly and exert its efficacy rapidly.

The present invention also provides a pharmaceutical composition, where a wetting agent can be added during the preparation of the pharmaceutical composition. The wetting agent can comprise at least one organic solvent, and can also comprise water, wherein the organic solvent can be an organic solvent with low toxicity, preferably ethanol and acetone and the like, and more preferably ethanol. The organic solvent can be present in an amount of 20-100%, preferably 50-95%, and more preferably 50-80% by weight, relative to the total weight of the wetting agent.

Since the wetting agent added during the preparation of the pharmaceutical composition comprises an organic solvent with low toxicity such as ethanol and the like, the resulting granules have a desired particle size distribution, and the dissolution of the active ingredient is rapid and complete, which facilitates the drug to exert its efficacy.

The pharmaceutical composition of the present invention dissolves rapidly and has a significant effect, and can be used for the treatment of cancers such as gastric cancer, lung cancer or breast cancer, etc.

The present invention also provides a method for preparing the pharmaceutical composition, comprising mixing (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof and cross-linked polyvinylpyrrolidone. The pharmaceutical composition can be prepared into granules by means of conventional methods in the art such as a wet granulation, and finally prepared into an oral formulation such as a tablet or capsule.

DETAILED DESCRIPTION OF THE INVENTION

The present invention will be further described in detail by the following examples and experimental examples. These examples and experimental examples are for illustrative purposes only and are not intended to limit the scope of the invention.

Example 1, Comparative Examples 1-4

The maleate salt of (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide (hereinafter referred to as compound A), lactose, microcrystalline cellulose, polyvinylpyrrolidone, and cross-linked polyvinylpyrrolidone were mixed in a ratio of Example 1 shown in Table 1. Wet granulation was carried out using an appropriate amount of 93.75 wt % ethanol solution in water as a wetting agent. The granules were dried until the moisture content was lower than 2%, and then dry milling was carried out. A prescription amount of magnesium stearate was added, and the mixture was mixed by a rotating mixer. The resulting total mixed granules were tableted and coated to prepare tablets. The tablets of Comparative Examples 1-4 that comprise low-substituted hydroxypropyl cellulose, sodium carboxymethyl starch, croscarmellose sodium, or starch were prepared according to the same method.

TABLE 1

| Components | Comparative Example 1 | Comparative Example 2 | Comparative Example 3 | Comparative Example 4 | Example 1 |
|---|---|---|---|---|---|
| Compound A | 31.1 | 31.1 | 31.1 | 31.1 | 31.1 |
| Lactose | 39.6 | 39.6 | 39.6 | 39.6 | 39.6 |
| Microcrystalline cellulose | 20.0 | 20.0 | 20.0 | 20.0 | 20.0 |
| Cross-linked polyvinylpyrrolidone | 0 | 0 | 0 | 0 | 5 |
| Low-substituted hydroxypropyl cellulose | 5 | 0 | 0 | 0 | 0 |
| Sodium carboxymethyl starch | 0 | 5 | 0 | 0 | 0 |
| Croscarmellose sodium | 0 | 0 | 5 | 0 | 0 |
| Starch | 0 | 0 | 0 | 5 | 0 |
| Polyvinylpyrrolidone | 3.3 | 3.3 | 3.3 | 3.3 | 3.3 |
| Magnesium stearate | 1.0 | 1.0 | 1.0 | 1.0 | 1.0 |
| Total | 100 | 100 | 100 | 100 | 100 |

Unit: weight %

Experimental Example 1: Dissolution Test

The dissolution tests of the tablets of Example 1 and Comparative Examples 1-4 were carried out according to the second method (paddle method) of the dissolution rate test described in the appendix of volume II of Chinese Pharmacopeia (2010 edition), using 900 ml of 0.1 mol/L hydrochloric acid solution as a dissolution medium at 37±0.5° C. and at the paddle speed of 50 rpm. The results showed that in the tablets of Example 1 that comprise cross-linked polyvinylpyrrolidone, the dissolution of compound A was rapid and complete, however in the tablets of Comparative Examples 1-4 that comprise low-substituted hydroxypropyl cellulose, sodium carboxymethyl starch, croscarmellose sodium or starch, the dissolution of compound A was slow and incomplete.

Figure 1:
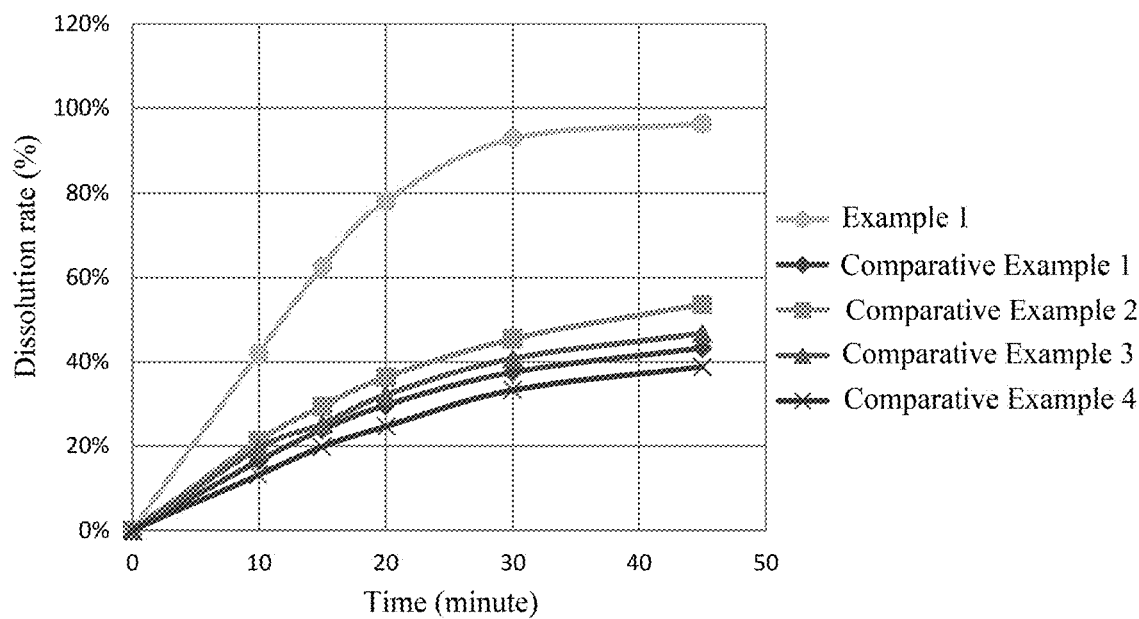
FIG. 1 shows the dissolution profiles of the tablets of Example 1 and Comparative Examples 1-4 in a 0.1 mol/L hydrochloric acid solution.

The dissolution profiles are shown in FIG. 1.

Examples 2-7

Compound A, lactose, microcrystalline cellulose, polyvinylpyrrolidone, and cross-linked polyvinylpyrrolidone were mixed in a ratio shown in Table 2. Wet granulation was carried out using an appropriate amount of 93.75 wt % ethanol solution in water as a wetting agent. The granules were dried until the moisture content was lower than 2%, and then dry milling was carried out. A prescription amount of magnesium stearate was added, and the mixture was mixed by a rotating mixer. The resulting total mixed granules were tableted and coated to prepare tablets.

TABLE 2

| Components | Example 2 | Example 3 | Example 4 | Example 5 | Example 6 | Example 7 |
|---|---|---|---|---|---|---|
| Compound A | 31.1 | 31.1 | 31.1 | 31.1 | 15.5 | 46.6 |
| Lactose | 42.6 | 36.6 | 29.6 | 24.6 | 52.2 | 21.1 |
| Microcrystalline cellulose | 20.0 | 20.0 | 20.0 | 20.0 | 20.0 | 20.0 |
| Cross-linked polyvinylpyrrolidone | 2 | 8 | 15 | 20 | 8 | 8 |
| Polyvinylpyrrolidone | 3.3 | 3.3 | 3.3 | 3.3 | 3.3 | 3.3 |
| Magnesium stearate | 1.0 | 1.0 | 1.0 | 1.0 | 1.0 | 1.0 |
| Total | 100 | 100 | 100 | 100 | 100 | 100 |

Unit: weight %

Experimental Example 2: Dissolution Test

The dissolution tests of the tablets of Examples 2-7 were carried out according to the second method (paddle method) of the dissolution rate test described in the appendix of volume II of Chinese Pharmacopeia (2010 edition), using 900 ml of 0.1 mol/L hydrochloric acid solution as a dissolution medium at 37±0.5° C. and at the paddle speed of 50 rpm. The results showed that in the tablets of Examples 2-5 that comprise cross-linked polyvinylpyrrolidone in different ratios and the tablets of Examples 6-7 that comprise compound A in different ratios, the dissolution of compound A was rapid and complete.

Figure 2:
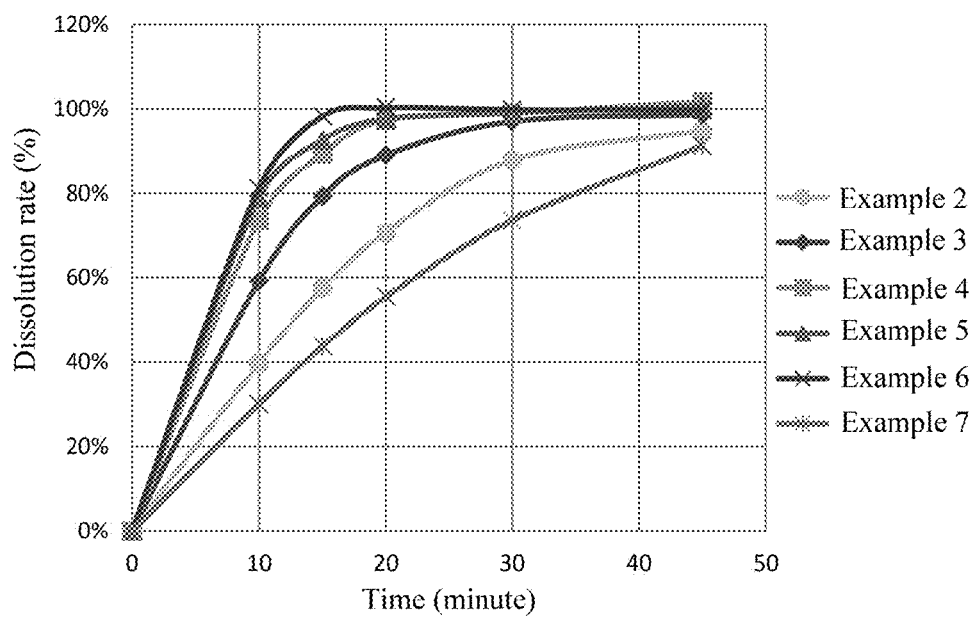
FIG. 2 shows the dissolution profiles of the tablets of Examples 2-7 in a 0.1 mol/L hydrochloric acid solution.

The dissolution profiles are shown in FIG. 2.

Examples 8-12, Comparative Example 5

Compound A, lactose, microcrystalline cellulose, polyvinylpyrrolidone, and cross-linked polyvinylpyrrolidone were mixed in a ratio shown in Table 3. Wet granulation was carried out using an appropriate amount of purified water, 20 wt % ethanol solution in water, 50 wt % ethanol solution in water, 80 wt % ethanol solution in water, 93.75 wt % ethanol solution in water and anhydrous ethanol respectively as a wetting agent. The granules were dried until the moisture content was lower than 2%, and then dry milling was carried out. A prescription amount of magnesium stearate was added, and the mixture was mixed by a rotating mixer. 100 g of the resulting total mixed granules were separated for sieving, and the rest of the granules were tableted and coated to prepare tablets.

TABLE 3

| Ingredients | Comparative Example 5 | Example 8 | Example 9 | Example 10 | Example 11 | Example 12 |
|---|---|---|---|---|---|---|
| Compound A | 31.1 | 31.1 | 31.1 | 31.1 | 31.1 | 31.1 |
| Lactose | 40.6 | 40.6 | 36.6 | 32.6 | 32.6 | 29.6 |
| Microcrystalline cellulose | 20.0 | 20.0 | 20.0 | 20.0 | 20.0 | 20.0 |
| Cross-linked polyvinylpyrrolidone | 8 | 8 | 8 | 8 | 8 | 8 |
| Polyvinylpyrrolidone | 3.3 | 3.3 | 3.3 | 3.3 | 3.3 | 3.3 |
| Magnesium stearate | 1.0 | 1.0 | 1.0 | 1.0 | 1.0 | 1.0 |
| Total | 100 | 100 | 100 | 100 | 100 | 100 |
| Wetting agent | Purified water | 20 wt % Ethanol | 50 wt % Ethanol | 80 wt % Ethanol | 93.75 wt % Ethanol | Anhydrous ethanol |

Unit: weight %

Experimental Example 3: Sieving Test 100 g of separated granules obtained in Examples 8-12 and Comparative Example 5 were shaken and sieved by using 50 mesh and 100 mesh screens. When purified water was used as a wetting agent in Comparative Example 5, there were a lot of large particle and fine powder in the resulting granule, and the particle size distribution was undesirable. When wetting agents comprising ethanol were used in Examples 8-12, there were less large particle and fine powder in the resulting granule, and the particle size distribution was more uniform.

Figure 3:
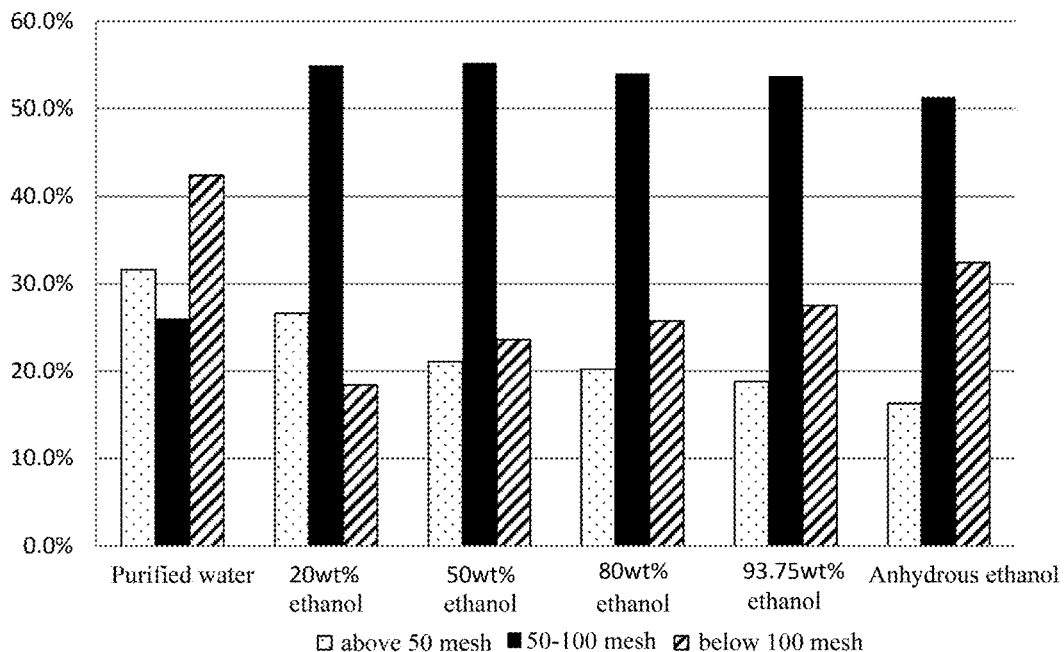
FIG. 3 shows the particle size distribution of Examples 8-12 and Comparative Example 5.
Figure 4:
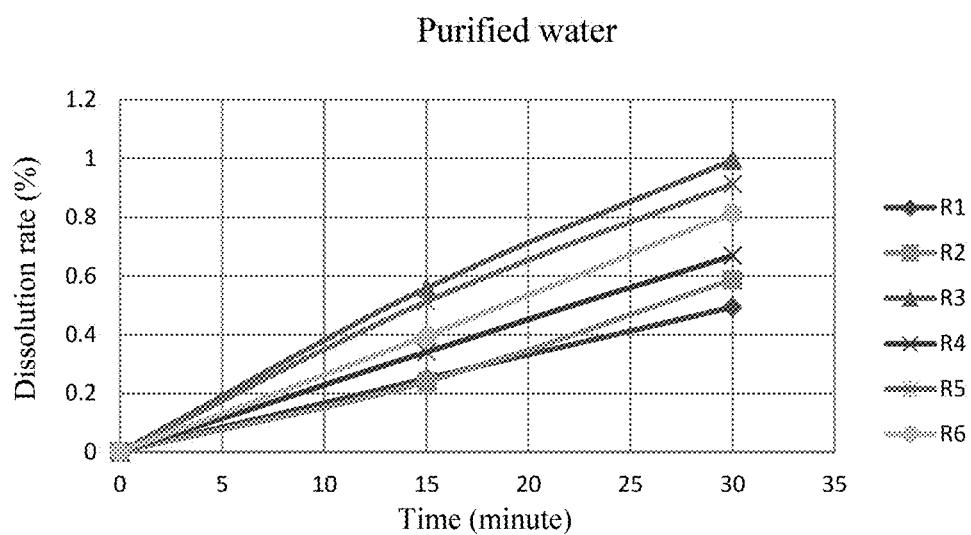
FIG. 4 shows the dissolution profiles of multiple tablet samples of Comparative Example 5 in a 0.1 mol/L hydrochloric acid solution.
Figure 5:
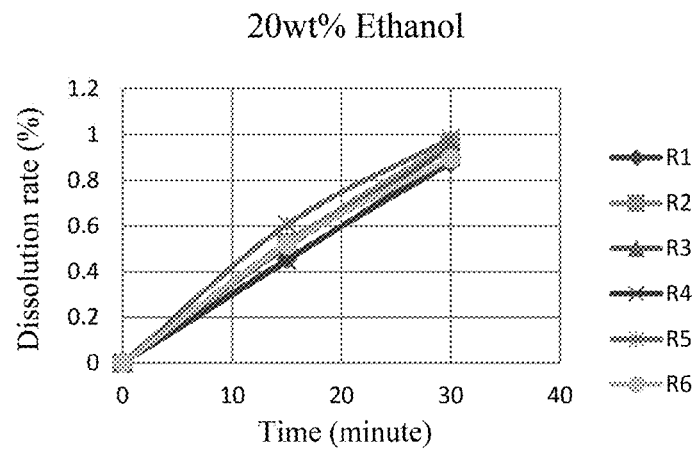
FIG. 5 shows the dissolution profiles of multiple tablet samples of Example 8 in a 0.1 mol/L hydrochloric acid solution.
Figure 6:
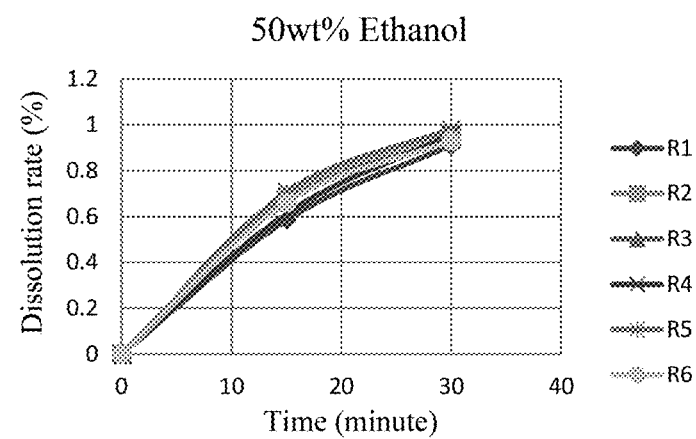
FIG. 6 shows the dissolution profiles of multiple tablet samples of Example 9 in a 0.1 mol/L hydrochloric acid solution.
Figure 7:
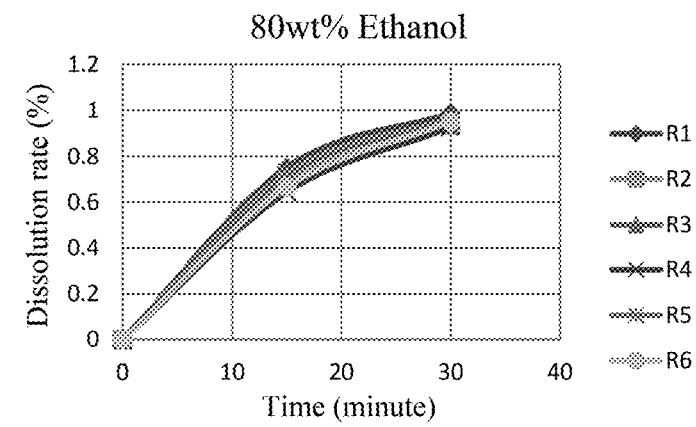
FIG. 7 shows the dissolution profiles of multiple tablet samples of Example 10 in a 0.1 mol/L hydrochloric acid solution.
Figure 8:
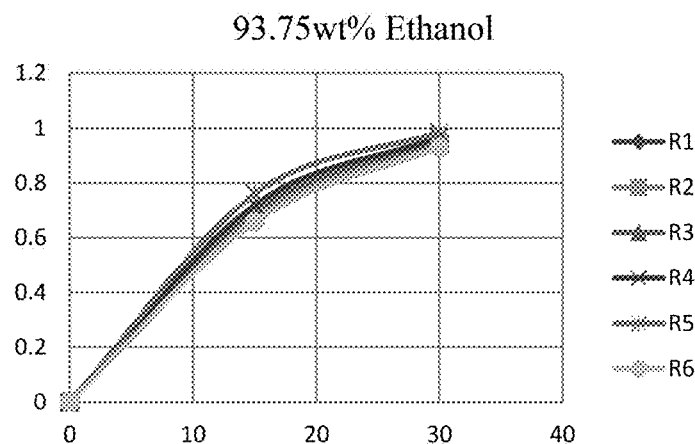
FIG. 8 shows the dissolution profiles of multiple tablet samples of Example 11 in a 0.1 mol/L hydrochloric acid solution.
Figure 9:
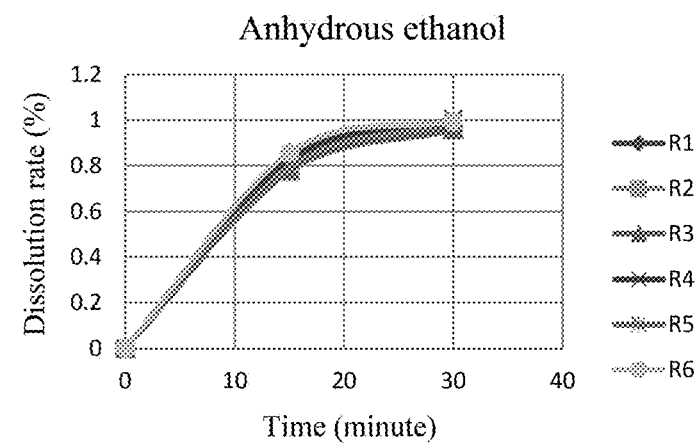
FIG. 9 shows the dissolution profiles of multiple tablet samples of Example 12 in a 0.1 mol/L hydrochloric acid solution.

The sieving results are shown in FIG. 3.

Experimental Example 4: Dissolution Test

The dissolution tests of the tablets of Examples 8-12 and Comparative Example 5 were carried out according to the second method (paddle method) of the dissolution rate test described in the appendix of volume II of Chinese Pharmacopeia (2010 edition), using 900 ml of 0.1 mol/L hydrochloric acid solution as a dissolution medium at 37±0.5° C. and at the paddle speed of 50 rpm. The results showed that when 20 wt % ethanol solution in water, 50 wt % ethanol solution in water, 80 wt % ethanol solution in water, 93.75 wt % ethanol solution in water and anhydrous ethanol were used respectively as a wetting agent in Examples 8-12, the resulting granules had a desirable particle size distribution, and the dissolution of compound A was rapid and complete; when purified water was used as a wetting agent in Comparative Example 5, in the resulting tablets, the dissolution uniformity of compound A was poor. When wetting agents comprising ethanol were used as wetting agents in Examples 8-12, in the resulting tablets, the dissolution uniformity of compound A was good.

The dissolution profiles are shown in FIGS. 4-9, and the R1-R6 shown in the figures represent tested samples Tablet 1-Tablet 6.

What is claimed is:

1. A pharmaceutical composition, comprising:
   1) an active drug that is (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof; and
   2) cross-linked polyvinylpyrrolidone.

2. The pharmaceutical composition according to claim 1, wherein the pharmacologically acceptable salt is a maleate salt.

3. The pharmaceutical composition according to claim 2, wherein the pharmacologically acceptable salt is a dimaleate salt.

4. The pharmaceutical composition according to claim 1, wherein the cross-linked polyvinylpyrrolidone is present in an amount of 2%-20% by weight, relative to the total weight of the composition.

5. The pharmaceutical composition according to claim 1, wherein the active drug is present in an amount of 5%-70% by weight, relative to the total weight of the composition.

6. The pharmaceutical composition according to claim 1, further comprising a binder, wherein the binder is one or more selected from the group consisting of hydroxypropyl methyl cellulose, hydroxypropyl cellulose, sodium carboxymethyl cellulose, polyvinylpyrrolidone, and methyl cellulose, and wherein the binder is present in an amount of 0.5%-15% by weight, relative to the total weight of the composition.

7. The pharmaceutical composition according to claim 1, further comprising a filler, wherein the filler is one or more selected from the group consisting of microcrystalline cellulose, calcium hydrogen phosphate, mannitol, pregelatinized starch, and lactose, and wherein the filler is present in an amount of 5%-80% by weight, relative to the total weight of the composition.

8. The pharmaceutical composition according to claim 1, further comprising a lubricant, wherein the lubricant is one or more selected from the group consisting of talc, magnesium stearate, zinc stearate, glyceryl behenate, sodium lauryl sulfate, hydrogenated vegetable oil, and colloidal silicon dioxide, and wherein the lubricant is present in an amount of 0.5%-5% by weight, relative to the total weight of the composition.

9. The pharmaceutical composition according to claim 1, wherein a wetting agent is used in preparation of the pharmaceutical composition, and wherein the wetting agent comprises at least one organic solvent.

10. The pharmaceutical composition according to claim 9, wherein the wetting agent further comprises water.

11. The pharmaceutical composition according to claim 9, wherein the organic solvent is ethanol or acetone.

12. The pharmaceutical composition according to claim 9, wherein the organic solvent is present in an amount of 20-100 wt %, relative to the total weight of the wetting agent.

13. The pharmaceutical composition according to claim 11, wherein the organic solvent is ethanol.

14. The pharmaceutical composition according to claim 1, wherein the pharmaceutical composition is an oral solid formulation.

15. The pharmaceutical composition according to claim 14, wherein the pharmaceutical composition is a tablet or a capsule.

16. A method of treating cancer, comprising administering to a subject in need thereof the pharmaceutical composition according to claim 1.

17. The method according to claim 16, wherein the cancer is gastric cancer, lung cancer, or breast cancer.

18. A pharmaceutical composition, comprising:
1) 5-70 wt % of (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or a pharmacologically acceptable salt thereof;
2) 2-20 wt % of cross-linked polyvinylpyrrolidone;
3) 5-80 wt % of a filler, wherein the filler is one or more selected from the group consisting of lactose and microcrystalline cellulose;
4) 0.5-15 wt % of a binder, wherein the binder is one or more selected from the group consisting of polyvinylpyrrolidone, hydroxypropyl methyl cellulose and hydroxypropyl cellulose; and
5) 0.5-5 wt % of a lubricant, wherein the lubricant is one or more selected from the group consisting of magnesium stearate and talc.

19. A method for preparing the pharmaceutical composition according to claim 1, comprising mixing (R,E)-N-(4-(3-chloro-4-(pyridin-2-ylmethoxy)phenylamino)-3-cyano-7-ethoxyquinolin-6-yl)-3-(1-methylpyrrolidin-2-yl)-propeneamide or the pharmacologically acceptable salt thereof and cross-linked polyvinylpyrrolidone.

* * * * *